United States Patent
Grass et al.

(10) Patent No.: US 6,606,514 B2
(45) Date of Patent: Aug. 12, 2003

(54) DEVICE FOR REPRODUCING SLICE IMAGES

(75) Inventors: Michael Grass, Hamburg (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 386 days.

(21) Appl. No.: 09/729,585

(22) Filed: Dec. 4, 2000

(65) Prior Publication Data

US 2002/0128551 A1 Sep. 12, 2002

(30) Foreign Application Priority Data

Dec. 2, 1999 (DE) .......................... 199 58 407

(51) Int. Cl.⁷ ................................ A61B 5/05
(52) U.S. Cl. ..................................... 600/427
(58) Field of Search ................. 600/427, 426, 600/425, 428, 429, 307, 308, 309, 310, 311, 312, 313, 314, 315

(56) References Cited

U.S. PATENT DOCUMENTS

| | | | | |
|---|---|---|---|---|
| 5,230,338 A | * | 7/1993 | Allen et al. ............... | 600/429 |
| 5,954,648 A | | 9/1999 | Van Der Brug ............. | 600/411 |
| 6,006,127 A | * | 12/1999 | Van Der Brug et al. ..... | 600/427 |
| 6,359,680 B1 | * | 3/2002 | Rubbert ...................... | 356/3.06 |
| 6,366,797 B1 | * | 4/2002 | Fisher et al. ................. | 600/410 |
| 6,377,837 B1 | * | 4/2002 | Coutts et al. ................ | 600/423 |
| 6,409,515 B1 | * | 6/2002 | Persohn et al. ............. | 434/262 |
| 6,434,507 B1 | * | 8/2002 | Clayton et al. ............. | 702/152 |
| 6,445,182 B1 | * | 9/2002 | Dean et al. .................. | 324/309 |
| 6,445,943 B1 | * | 9/2002 | Ferre et al. ................. | 600/424 |
| 6,470,204 B1 | * | 10/2002 | Uzgiris et al. .............. | 600/411 |
| 6,497,134 B1 | * | 12/2002 | Faul et al. .................... | 73/1.81 |

* cited by examiner

*Primary Examiner*—Daniel Robinson
(74) *Attorney, Agent, or Firm*—John Vodopia

(57) ABSTRACT

The invention relates to a device for reproducing slice images during the treatment of an object to be examined, the device includes measuring hardware for determining, relative to a reference system, the position of a medical instrument partly introduced into the object to be examined during the treatment. In order to enable such a device to change the orientation of slice images during the treatment in a simple and interactive manner, according to the invention adjusting means are provided on the part of the medical instrument which projects from the object to be examined in order to change the orientation of the slice images reproduced. The invention also relates to a medical instrument appropriately constructed for this purpose and provided with such adjusting means as well as to an appropriate method.

16 Claims, 2 Drawing Sheets

DEVICE FOR REPRODUCING SLICE IMAGES

BACKGROUND OF THE INVENTION

Figure 1:
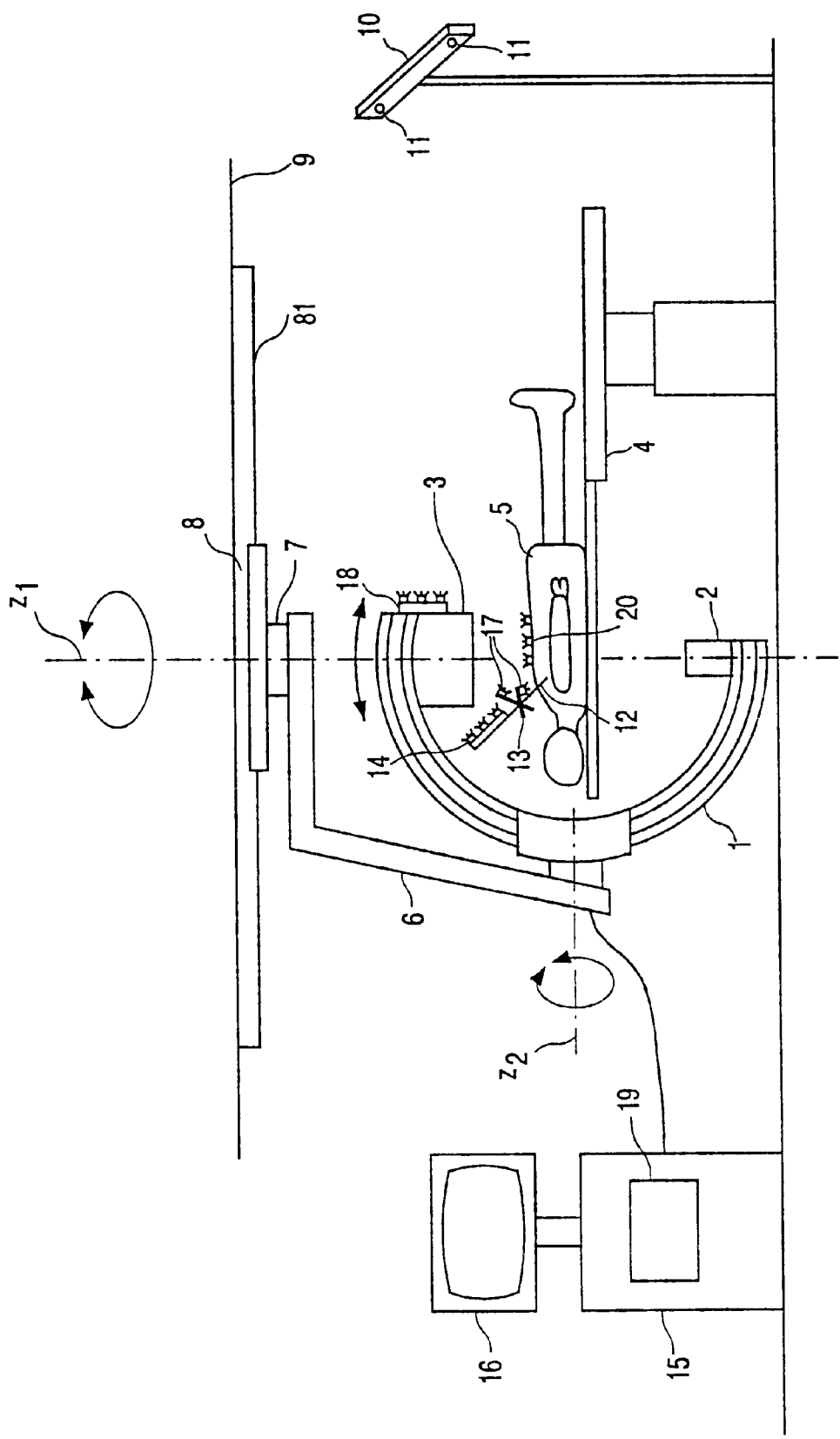

The invention relates to a device for reproducing slice images during treatment of an object to be examined, as well as to a medical instrument to be inserted partly into an object to be examined during a treatment. The invention also relates to a corresponding method for forming slice images.

A device and a method of the kind set forth are known from U.S. Pat. No. 5,954,648. Therein, the position of a medical treatment instrument, for example a biopsy needle, is determined by means of an optical position measuring system and reproduced in X-ray slice images pre-operatively formed by means of an X-ray device. To this end, the medical instrument is provided with LEDs whose position in space can be determined by means of a camera of the position measuring system. A suitable registration method can be applied so as to convert such positions in space into positions relative to the imaging geometry of the X-ray device and hence relative to the X-ray slice images.

When use is made of such a device, notably for image-guided surgery, the attending physician is offered one or more slice images in which the instantaneous position of the medical instrument is reproduced so as to facilitate the guiding of the instrument within the object to be examined. The orientation and position of the images shown are fixed at the beginning; for example, each time a slice image is displayed which is situated in a plane whereto the medical instrument extends at right angles and which extends through the tip of the medical instrument. The position of the slice image reproduced is then moved along, for example, with the medical instrument or varied by entry into a control computer. However, it would be attractive if the position and orientation of the slice images reproduced could be adjusted quickly, simply and notably interactively by the attending physician himself or herself, so that the physician can always obtain an impression of the anatomy of the object to be examined itself.

OBJECTS AND SUMMARY OF THE INVENTION

Therefore, it is an object of the invention to modify a device of the kind set forth so as to enable simple, fast and interactive variation of the position and orientation of the slice images reproduced. It is also an object to propose a medical instrument and a method appropriate for said device.

The object for reproducing slice images during treatment of an object to be examined, which device includes measuring means for determining, relative to a reference system, the position of a medical instrument partly inserted into the object to be examined during the treatment, wherein adjusting means are provided on a part of the medical instrument which projects from the object to be examined after its insertion therein, which adjusting means are arranged to change the orientation of the slice images reproduced The invention is based on the recognition of the fact that appropriate adjusting means for changing the orientation of the slice images reproduced should be arranged in a location where the attending physician can simply and interactively change their adjustment. In the case of an intervention by means of a medical instrument, this location is the medical instrument itself. A change of the adjustment of such adjusting means thus enables direct reproduction of a differently oriented slice, with as little delay as possible. For example, the angle between a slice extending through the tip of the medical instrument and the longitudinal axis of the medical instrument can be varied. Alternatively, a slice extending through the longitudinal axis of the medical instrument can be rotated about the medical instrument. The slice images reproduced themselves can be formed either from a three-dimensional, pre-operatively acquired image data set, acquired by means of a suitable imaging device such as an X-ray device, a computed tomography apparatus, a magnetic resonance tomography apparatus or an ultrasound device, or be acquired intra-operatively by means of such an imaging device during the treatment.

The adjusting means in a further embodiment of the invention are coupled to a control unit, for example via a wired connection or a wireless link, in order to apply the instantaneous adjustment of the adjusting means to the control unit and hence influence the reproduction and possibly previous formation of the slice images.

The adjusting means in an alternative embodiment of the invention are constructed in such a manner that their adjustment can be determined by means of the measuring means. For example, when use is made of a known optical position measuring system, as envisaged in a further embodiment of the invention, the adjusting means may be provided, like a medical instrument itself, with LEDs whose positions in space can be determined, thus enabling adjustment of the adjusting means. Such a position measuring system preferably utilizes infrared LEDs and infrared cameras; however, there are also other possibilities such as electromagnetic receivers and transmitters.

The embodiments of the invention as disclosed in the claims 4 to 6 are intended to enable as simple and easy as possible operation of the adjusting means. Preferably, a value characterizing the orientation of a slice image reproduced, for example the angle between a slice reproduced and a reference slice, should also be readable on the basis of the adjusting means.

The adjusting means include a rotary switch. The rotary switch includes two pins that are arranged in a cross-like arrangement so as to extend perpendicularly to the longitudinal axis of the medical instrument, the pins being rotatable about the longitudinal axis of the medical instrument and indicating the orientation of two slice images reproduced, each of said slice images being situated in a plane defined by the longitudinal axis of the medical instrument and a pin axis extending through a pin adjusting means. Adjusting means of this kind can be simply manufactured, can be readily operated and, if necessary, can be simply provided on and removed from existing medical instruments.

Slice images extending through the longitudinal axis of the medical instrument are reproduced in a preferred embodiment. Such slice images can be rotated about said longitudinal axis by means of the adjusting means.

In a preferred embodiment in which an X-ray device is provided, slice images formed from a pre-operatively acquired image data set as well as intra-operatively formed X-ray slice images or in X-ray projection images can be reproduced. The adjusting means may be constructed in such a manner that the orientation of the intra-operatively formed X-ray images as well as the slice images formed from the pre-operatively acquired image data set can be influenced. The adjusting means are thus also capable of controlling the formation of X-ray images by means of the X-ray device which may be, for example, a C-arm X-ray device.

The adjusting means are constructed so that they can be reproduced in the X-ray images, the measuring means being constructed in such a manner that the adjustment of the adjusting means can be determined from the reproduction of the adjusting means. A separate position measuring system as described above can be dispensed with in such a further embodiment. The position of the medical instrument relative to the pre-operatively acquired image data set and the instantaneous adjustment of the adjusting means are then determined by reproducing at least a part of the medical instrument and the adjusting means in intra-operatively acquired X-ray images, for example X-ray projection images. Using a suitable registration method, the position of the medical instrument is determined from such X-ray images which are formed, for example, at fixed time intervals, during a treatment the adjustment of the adjusting means then being "read". To this end, the adjusting means are preferably constructed and the X-ray images are formed in such a manner that the determination of the adjustment is unambiguously and simply possible, so that such determination can also be performed in a computer-aided fashion.

The invention also covers a medical instrument appropriately configured for use in conjunction with a device according to the invention. The medical instrument is provided notably with suitable adjusting means which may be constructed as described above.

BRIEF DESCRIPTION OF THE DRAWING FIGURES

Figure 2A:
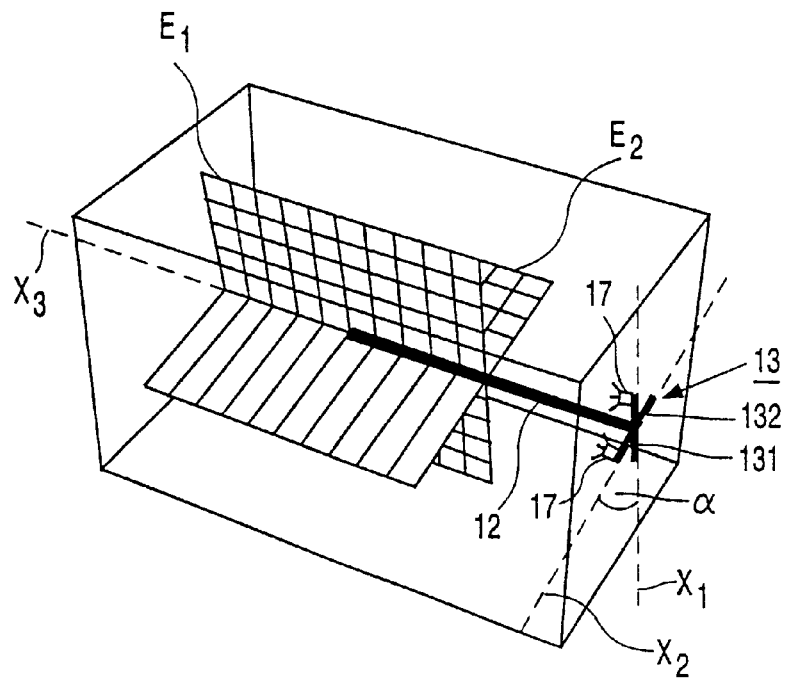
Figure 2B:
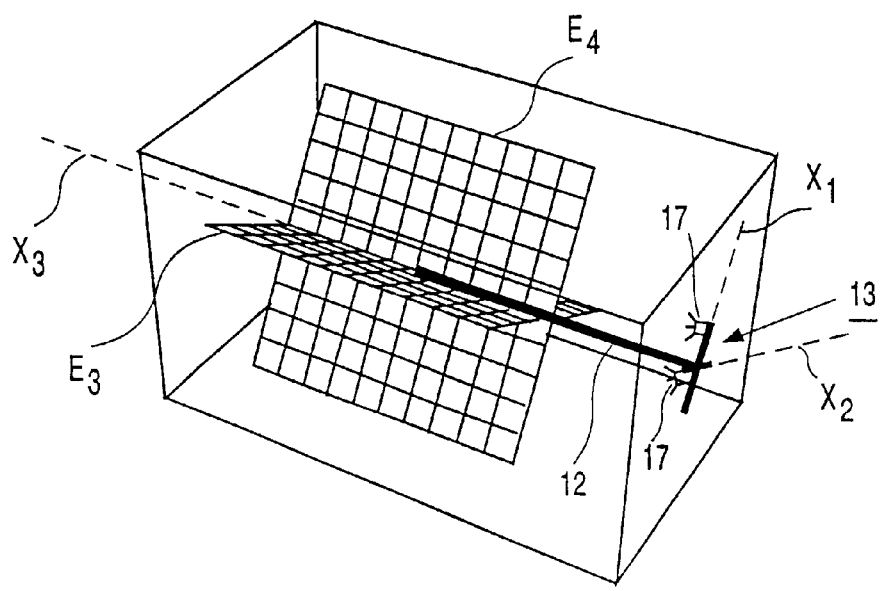

The invention will be described in detail hereinafter with reference to the drawings. Therein:

FIG. 1 shows a device according to the invention which includes an X-ray device and a position measuring system, and FIGS. 2a, 2b show a medical instrument according to the invention in two different orientations.

DETAILED DESCRIPTION OF THE INVENTION

The device according to the invention as shown in FIG. 1 includes an X-ray device with a C-arm 1 with an X-ray tube 2 arranged at a first end and an X-ray detector 3, for example an image intensifier, arranged at its other end. Such an X-ray device is suitable for forming X-ray projection images of a patient 5, arranged on a table 4, from different X-ray positions; to this end, the C-arm 1 is constructed so as to be rotatable about three axes in space, that is, $z_1$, $z_2$ and (not shown) $z_3$. The C-arm 1 is attached to the ceiling 9 via a supporting device 6, a pivot 7 and a slide 8 which is displaceable in the horizontal direction in a rail system 81.

Furthermore, a position measuring system of the known kind is provided with a camera unit 10 with two infrared cameras 11. The position in space of infrared light-emitting diodes, that are present in the examination zone can be determined by means of said camera unit 10. Three of such light-emitting diodes 14 are provided on a medical instrument 12, partly introduced into the patient 5 during the treatment thereof, in order to measure the position of the medical instrument 12 in space and to convert it into a position of the medical instrument 12 relative to a three-dimensional image data set of the examination zone of the patient 5 which has been pre-operatively acquired by means of the X-ray device shown. The medical instrument 12 constructed in conformity with the invention is also provided with adjusting means 13 whose construction and operation will be described in detail hereinafter. The adjusting means 13 are also provided with light-emitting diodes 17 for determining the instantaneous adjustment of the adjusting means 13 by means of the position measuring system. In order to determine also the position of the imaging unit of the X-ray device and the position of the patient, three light-emitting diodes 13 are provided on the X-ray detector 3 and further light-emitting diodes 20 are attached to the patient 5.

A control unit 15 controls the X-ray device and the position measuring system. The control unit 15 also receives the data acquired (X-ray images, position data) so as to be processed in an arithmetic unit 19. Various images can be displayed on a monitor 16 in order to assist the physician during the intervention.

The X-ray device shown is suitable for forming a series of X-ray projection images from different X-ray positions prior to an intervention in order to derive therefrom a three-dimensional image data set, three-dimensional reconstruction images and X-ray slice images therefrom, as well as for forming X-ray projection images during the intervention. Because each time the position of the imaging unit is also determined, the position of intra-operatively acquired X-ray projection images can also be determined relative to a pre-operatively determined image data set. The position of the medical instrument 12 relative to the pre-operatively acquired image data set can also be determined in this manner. The instantaneous position of the medial instrument 12 can thus be reproduced in slice images formed from the pre-operatively acquired image data set and displayed on the monitor 16 during the intervention.

In order to realize this functionality, it is usually necessary to provide special markers on the patient so as to acquire the pre-operative image data set; these markers are also reproduced in the images and must still be present in the same locations during the treatment. Using a special pointer whose position in space can be determined by means of the position measuring system, these markers are then individually approached in order to determine their positions in space. The position of the pre-operative image data set in the space co-ordinate system or in the patient co-ordinate system is thus determined.

The orientation of such slice images can be simply changed manually and interactively by the physician during the treatment of the patient 5; this operation is performed by means of the adjusting means 13 and will be described in detail hereinafter with reference to the FIGS. 2a and 2b. These Figures show a medical instrument 12, for example a thoroughly simplified biopsy needle, the adjusting means 13 being provided at the end thereof. The adjusting means include two short pins 131 and 132 which are arranged perpendicularly to one another and to the longitudinal axis $x_3$ of the medical instrument 12. An infrared light-emitting diode 17 is provided on each of said pins 131, 132; the position of these diodes can be determined by means of the position measuring system. The pins 131 and 132 are constructed in such a manner that they are rotatable about the longitudinal axis $x_3$ of the medical instrument 12 in the plane defined by their two longitudinal axes $x_1$, $x_2$, be it that the angle $\alpha$ between the two pins 131, 132 is fixed.

The physician can observe two X-ray slice images on the monitor during a treatment, said images extending in the two planes $E_1$ and $E_2$ through the medical instrument 12. The planes $E_1$, $E_2$ are defined by the longitudinal axis $x_3$ of the medical instrument 12 and the longitudinal axis $x_1$ or $x_2$ of one of the two rods 131, 132 so that they extend perpendicularly to one another in the case shown. During the treatment, however, it may be useful to change the orientation of the displayed slice images in order to observe the anatomy surrounding the medical instrument 12 from a different perspective. In order to do so, the physician need merely rotate the adjusting means 13 that are constructed as a cross. The LEDs 17 provided on the pins 131 and 132 then also reach a different position; this is detected by means of the position measuring system. This information is applied directly to the control unit 15 and the arithmetic unit 19 so that immediately new slice images are formed and displayed on the monitor 16, said new slice images now being situated in the planes $E_3$ and $E_4$ (see FIG. 2b) defined by the axes $x_2$, $x_3$ and $x_1$, $x_3$, respectively.

It is also feasible to construct the adjusting means 13 so as to be pivotable, that is, in such a manner that the angle between the longitudinal axis $x_3$ of the instrument 12 and the plane defined by the pins 131 and 132 can be changed. In that case it would be possible to display, for example, each time the slice that extends through the tip of the instrument 12 and is situated parallel to the plane defined by the pins 131 and 132.

It may be arranged that the X-ray device shown also forms X-ray projection images during a treatment, which projection images are reproduced separately or combined with the pre-operatively acquired image data set. Furthermore, it may be arranged that the position of the C-arm is also changed after a change of the adjustment of the adjusting means 13 so that a new X-ray projection image is formed from a different perspective.

The Figures show merely exemplary embodiments of a medical instrument according to the invention as well as a device according to the invention. A number of alternatives exist in respect of notably the construction of the adjusting means. In the arrangement shown in FIG. 1 the position measuring system with the camera unit and the light-emitting diodes can be completely dispensed with when the part of the medical instrument with the adjusting means is reproduced in X-ray projection images at regular, time intervals during the treatment and the instantaneous adjustment of the adjusting means can be derived therefrom. Another embodiment of the device according to the invention is constructed in such a manner that no X-ray device (or another imaging device) is involved during the treatment, but only a position measuring system for determining the instantaneous position of the medical instrument and the instantaneous adjustment of the adjusting means as well as an image processing unit with an image memory in which a pre-operatively acquired image data set is stored.

What is claimed is:

1. A device for reproducing slice images during treatment of an object to be examined, which device includes measuring means for determining, relative to a reference system, the position of a medical instrument partly inserted into the object to be examined during the treatment, wherein adjusting means (13) are provided on a part of the medical instrument which projects from the object to be examined after its insertion therein, which adjusting means are arranged to change the orientation of the slice images reproduced.

2. A device as claimed in claim 1, wherein the adjusting means are coupled to a control unit (15) which controls the reproduction of the slice images.

3. A device as claimed in claim 1, wherein the adjusting means are constructed in such a manner that their adjustment can be determined by means of the measuring means.

4. A device as claimed in claim 1, characterized in that the adjusting means are constructed in such a manner that their adjustment can be simply changed manually.

5. A device as claimed in claim 1, wherein the adjusting means include a rotary or sliding device whose adjustment indicates and determines the orientation of the slice images reproduced.

6. A device as claimed in claim 1, wherein the adjusting means include a rotary switch which is arranged at the area of the grip of the medical instrument.

7. A device as claimed in claim 6, wherein the rotary switch includes two pins that are arranged in a cross-like arrangement so as to extend perpendicularly to the longitudinal axis ($x_3$) of the medical instrument, the pins being rotatable about the longitudinal axis ($x_3$) of the medical instrument and indicating the orientation of two slice images reproduced, each of said slice images being situated in a plane defined by the longitudinal axis ($x_3$) of the medical instrument and a pin axis ($x_1$, $x_2$) extending through a pin.

8. A device as claimed in claim 7, wherein the angle ($\alpha$) between the two pins can be varied.

9. A device as claimed in claim 7, wherein the angle ($\alpha$) between the two pins amounts to 90°.

10. A device as claimed in claim 1, wherein the orientation of the slice images reproduced is determined by the longitudinal axis ($x_3$) of the medical instrument and the adjustment of the adjusting means.

11. A device as claimed in claim 1, wherein the measuring means include a position measuring system, notably an optical position measuring system, for determining the spatial positions of the medical instrument and the adjusting means.

12. A device as claimed in claim 1, wherein the slice images are formed from a three-dimensional image data set, notably an X-ray image data set, acquired prior to the treatment.

13. A device as claimed in claim 1, wherein there is provided an X-ray device, for forming X-ray images during the treatment, and that the orientation of the X-ray images and the slice images can be changed by means of the adjusting means.

14. A device as claimed in claim 13, wherein the adjusting means are arranged so as to be reproducible in the X-ray images and that the measuring means are constructed in such a manner that the adjustment of the adjusting means can be determined from the images of the adjusting means.

15. A medical instrument to be introduced partly into an object to be examined during a treatment, the formation of slice images of the object to be examined during the treatment being desired, wherein, in order to change the orientation of the slice images formed adjusting means are provided on a part of the medical instrument which projects from the object to be examined after its introduction therein.

16. A method of reproducing slice images during the treatment of an object to be examined, measuring means being used for determining, relative to a reference system, the position of a medical instrument partly inserted into the object to be examined during the treatment, wherein the adjustment of adjusting means provided on the part of the medical instrument which projects from the object to be examined is changed in order to change the orientation of the slice images reproduced.

* * * * *